United States Patent
Morrison et al.

(10) Patent No.: US 6,194,617 B1
(45) Date of Patent: *Feb. 27, 2001

(54) LITHIUM TERTIARY ALKOXIDES

(75) Inventors: Robert C. Morrison; Conrad W. Kamienski, both of Gastonia; James A. Schwindeman, Charlotte, all of NC (US)

(73) Assignee: FMC Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/762,071

(22) Filed: Dec. 9, 1996

Related U.S. Application Data

(60) Division of application No. 08/437,268, filed on May 8, 1995, now Pat. No. 5,583,269, which is a continuation-in-part of application No. 08/129,818, filed on Sep. 30, 1993, now abandoned.

(51) Int. Cl.$^7$ ........................................................ C07C 3/30
(52) U.S. Cl. ................................................................ 568/851
(58) Field of Search ............................................. 568/851

(56) References Cited

U.S. PATENT DOCUMENTS

| 3,761,529 | 9/1973 | Drahaoslav | 568/851 |
| 3,971,833 | 7/1976 | Lenz et al. | 568/851 |

*Primary Examiner*—Michael L. Shippen
(74) *Attorney, Agent, or Firm*—Alston & Bird LLP

(57) ABSTRACT

A process for quickly preparing easily separable solutions of lithium tertiary-alkoxides. Comprising the steps of reacting lithium metal in bulk solid form, containing less than 0.1% by weight of sodium, with a tertiary alcohol in mole ratios of metal to alcohol ranging from 2 to 1 to 10 to 1 in a solvent selected from ethereal or hydrocarbon solvents under an inert atmosphere at elevated temperature for 1 to 10 hours, cooling the product and separating the product solution from the unreacted lithium metal in the reactor, and optionally adding solvent and sufficient lithium metal and alcohol to said unreacted metal in said reactor to maintain said mole ratio of lithium metal to alcohol, and continuing the reaction, thereby to form further lithium tert-alkoxide, and repeating said steps a number of times.

9 Claims, No Drawings

LITHIUM TERTIARY ALKOXIDES

This application is a divisional of application Ser. No. 08/437,268, filed May 8, 1995, now U.S. Pat. No. 5,583,269.

This application is a continuation-in-part of application Ser. No. 08/129,818 filed Sep. 30, 1993, now abandoned.

This invention concerns a process for preparing lithium tertiary alkoxides by reacting lithium metal in gross or bulk form with a tertiary alcohol.

Alkali metal alkoxides and especially alkali metal tertiary alkoxides such as lithium tertiary butoxide are used in the preparation of pharmaceutical intermediates and in the synthesis of polymers and in general organic synthesis. In co-pending application U.S. Ser. No. 08/973,116 filed Nov. 6, 1992 now U.S. Pat. No. 5,276,219, there is a described a process for preparing clear, suspensoid-free solutions of lithium tert-butoxide in tetrahydrofuran at reflux by reaction of lithium metal in finely divided dispersed particle form with an excess of tert-butyl alcohol.

Although lithium metal in a finely divided dispersed state reacts rapidly with tert-butyl alcohol in THF medium, it is costly to produce, requiring the steps of (a) heating of bulk lithium metal and mineral oil to about 190–200° C. in the presence of a dispersion aid, such as oleic acid, (b) stirring the resultant molten mixture at high speeds in a special dispersion unit to produce the required small particle sizes (generally less than 100 microns), then (c) cooling the product (preferably without stirring), and then finally (d) removing the mineral oil from the solidified lithium metal particles by washing several times with a volatile hydrocarbon solvent, such as hexane or pentane. The volatile hydrocarbon solvent can optionally be removed by purging with an inert gas such as argon, or more preferably, be washed one or more times with tetrahydrofuran before reaction with the tert-butyl alcohol.

Besides being costly to produce, lithium dispersion also may add undesirable impurities to the subsequent lithium tert-butoxide product in THF such as, e.g., mineral oil and oleic acid breakdown products, and volatile hydrocarbons.

Because of the extremely small sizes of the lithium metal particles, a high proportion of solid impurities, small in size, are generally present after reaction with the alcohol is complete. Impurities on the lithium surface slow down the initial reaction. These impurities arise from side reactions with traces of oxygen in the inert atmosphere, of traces of water in the solvent and alcohol, and with the solvent itself. These small solid impurities (including any unreacted lithium metal particles) cause filtration problems, although the use of an excess of the alcohol generally takes care of any unreacted lithium metal.

The present invention provides a process for quickly preparing easily separable solutions of lithium tert-alkoxides in an economically feasible time period (1 to 10 hours), comprising the steps of: reacting lithium metal in bulk solid form, containing less than 0.1% by weight of sodium, with a tertiary alcohol in mole ratios of lithium metal to alcohol ranging from 1 to 1 to 10 to 1 in an ethereal or hydrocarbon medium under an inert atmosphere at elevated temperature between 25 and 100° C., cooling the product and separating the product solution from the unreacted lithium metal in the reactor; the process is conveniently continued when higher mole ratios of lithium to alcohol (>2) are employed by adding additional solvent, sufficient lithium metal and alcohol to the unreacted metal in the reactor to maintain the mole ratio of lithium metal to alcohol, and continuing the reaction, thereby to form further lithium tert-alkoxide, and repeating said steps a number of times. Optionally the reaction may be catalyzed with small amounts of a $C_1$ to $C_3$ alcohol. "Bulk" form is defined herein as lithium metal obtained as castings, or pieces thereof, from manufacture in an electrolytic cell, or from an extrusion process, including subsequent cutting into smaller, more manageable pieces or even by directly slicing the cell "ingot" into smaller pieces but generally not smaller than 0.5 grams. These pieces of bulk lithium have volumes of at least one cubic centimeter. It should be noted that the bulk metal is maintained in solid form throughout the reaction although the pieces diminishes somewhat in size. The metal is never reacted in a liquified form (as per Lenz in U.S. Pat. No. 3,971,833). It is known that in liquified form, the metal (sodium) is reduced to a particulate form by the reactant alcohol and is not reacted in bulk form (as per Alkali Metal Dispersions, by I. Fatt & M. Tashima, D. van Nostrand, Inc., Princeton, N.J., 1961 page 80, ref. 108). In addition, the high reaction temperature required to dissociate the alcohol of complexation with sodium alkoxides is not required when the alkali metal is lithium and could be detrimental because of the ease of sublimation of lithium tert-butoxide at 200° C. and potential pyrolysis of the product.

Unexpectedly, the process of the present invention overcomes problems experienced with the use of lithium metal in a finely divided (dispersed) state without experiencing an overly great increase in reaction time by the use of a sufficient excess of lithium metal in bulk form (over and above the alcohol used) in the essential absence of any hydrocarbon or other (solid) impurities. Impurities on the lithium surface slow down the initial reaction. Surprisingly, the amount of lithium metal in bulk form needed to preserve a comparable overall reaction time when compared to lithium in dispersed form is only in the order of about three times. For example, the surface area of one gram equivalent of lithium metal particles 20 microns in diameter is about 13,000 square centimeters, while the surface area of an equivalent amount of lithium metal cubes with dimensions of one centimeter by one centimeter by one centimeter is only 79 square centimeters, a one hundred sixty-six times greater surface area for the dispersed lithium. One would therefore expect the relative amount of lithium in bulk form needed to give a overall reaction rate comparable to the dispersed lithium to be in the order of one hundred sixty-six times greater. Instead, only three equivalents of lithium metal in the form of cubes was found to react with one equivalent of the alcohol in a comparable overall time (180 minutes) as did one equivalent of lithium metal dispersed to 20 micron diameter particles (135 minute overall reaction time). Although the sizes of the solid bulk lithium metal pieces are reduced somewhat in size during reaction, the amount of excess lithium metal employed is such as to cause this size reduction to be minimal. Resupply of the equivalent (s) of metal lost in each reaction maintains this state for a great number of runs. See Table I. Lithium tertiary butoxide in the tables I–V is abbreviated as LTB and elsewhere as lithium tert-butoxide and lithium t-butoxide.

After the reaction of one of the three equivalents of the bulk lithium metal is completed, the slightly hazy product solution can be easily decanted from the unreacted (floating) lithium metal and filtered quickly. Another reaction can be started in the same reactor, adding only another equivalent each of lithium metal and alcohol and the required amount of solvent. When the process is to be repeated one or more times in the same reactor it is advantageous to immediately add additional solvent after the product of the preceding reaction is recovered. Surprisingly, the overall reaction time decreases still further in the second run (130 minutes) and then stays constant for the next two consecutive runs (120 minutes). This decrease in time is thought to be due to preconditioning of the lithium metal. (Removal of surface impurities).

The use of only one equivalent or slightly greater than one equivalents of bulk lithium metal especially if the lithium contains an appreciable amount of sodium (0.1%) slows the reaction rate inordinately and makes the recovery of high yields of lithium tert-alkoxide impractically low (see, e.g. Lockman and see the comparative example Table 3).

The ease of separation of the product solution from unreacted lithium metal is maintained in each subsequent run and there is no hazardous unreacted lithium to be disposed of as in the runs using dispersed lithium.

The key factor contributing to the effective use of bulk solid lithium metal in the preparation of lithium alkoxides such as lithium tert-butoxide has unexpectedly been found to lie in the content of sodium metal dissolved in the lithium metal. Whereas, sodium content plays a small, albeit significant, role in the preparation of these alkoxides when lithium metal in a dispersed form is employed, the sodium level in bulk metal plays a preeminent role in their preparation.

It is known that elevated sodium levels in the lithium metal used in preparing alkyllithiums are beneficial. For example W. N. Smith, Jr., in *Journal of Organometallic Chemistry*, 82 (1974) 1–6 recommends the use of of 1% by weight of sodium in the lithium metal used to prepare tertiary butyllithium from tert-butyl chloride. It is also stated that lower levels of sodium (0.02%) in the lithium metal resulted in no reaction with the alkyl chloride. It has now unexpectedly been found that sodium levels beneficial to the preparation of alkyllithiums (in the range of 0.1 to 1.0% sodium) are actually detrimental to the preparation of lithium tert-alkoxides such as lithium tert-butoxide in ethereal and hydrocarbon media at relatively mild temperatures (35–100° C.). In the case where bulk solid lithium metal is employed, inordinately long reaction times (in the order of days) are required to achieve high conversions of alcohol to product alkoxide, even when multiple equivalents of metal to alcohol (3 to 1) are present. On the other hand, when sodium content of bulk solid lithium metal is kept low, i.e., below 0.01 percent, the reaction rates are speeded up considerably and conversion is complete in less than four hours, even with the use of only one equivalent of the metal. As mentioned above, the use of multiple equivalents (e.g. 3) of lithium metal per equivalent of alcohol still further speed up the reaction rate, so that conversion to product is complete in less than two hours, especially with preconditioned metal. However, only one equivalent of metal per alcohol is actually required.

In addition, the lithium alkoxide products generated from low sodium grade bulk lithium metal are themselves low in sodium content and are thus purer than lithium alkoxides produced high sodium ("catalytic grade") containing lithium metal used in either bulk or dispersed forms. Thus, a typical catalytic grade lithium metal containing about 0.5 weight percent sodium will produce a lithium tert-butoxide solution (20 weight percent in THF) containing about 90 ppm sodium, whereas a typical low sodium grade lithium metal containing about 0.005 weight percent sodium will result in an equivalent lithium tert-butoxide solution containing less than one ppm of sodium, i.e., an essentially sodium-free solution.

In another embodiment of the invention, certain catalysts are used to speed up the overall reaction time of bulk lithium metal pieces with tert-butyl alcohol in THF solution. With a mole ratio of t-butyl alcohol to lithium metal of 1.1, addition of small amounts (2–5 mole % based on tert-butyl alcohol) of C1 to C3 alcohols decreases the reaction time by about one-half when using lithium metal rod pieces (1.27 centimeter diameter by one centimeter long). The ratio of lithium metal to tert alcohol can be 0.9 to 1 to 10 to 1.

It is quite unexpected that the size of the metal pieces used in the reaction with tert-butyl alcohol in tetrahydrofuran can be varied widely, depending on the batch size of the runs, without unduly affecting [reducing] the overall reaction time. Thus, any of the common commercially available sizes of lithium metal may be employed or segments [pieces] may be cut from these. For example, in a forty gallon size run to prepare 184 moles of product, ten one inch thick trapezoidal-shaped pieces of lithium were cut from each of four two pound trapezoidal ingots having dimensions of 2.5/3.5 inches (6.4/8.9 cm) in width by 3.25 inches (8.3 cm) in height by 10.5 inches (26.7 cm) in length, and charged to the reactor, along with the requisite amount of tert-butyl alcohol (mole ratio Li/ROH=3) and THF solvent. The mixture was heated to reflux and required 4–5 hours to completion [average conversion of alcohol of 99+% over seven consecutive runs]. This overall reaction time compares favorably to one mole laboratory runs using much smaller pieces of metal [see Table VI, P.P. Series 6].

Sizes of lithium metal available commercially are: one inch (2.5 cm) diameter by 8 inch (20.3 cm) long rods, one-half inch 1.3 cm) by 6.5 inch (16.5 cm) long rods, 2.25 inch (5.7 cm) by 3.38 inch (8.6 cm) long cylindrical ingots [¼ lb], 3 inch (7.6 cm) diameter by 3.8 inch (9.7 cm) long cylindrical ingots [½ lb (227 g)], 4 inch (10.2 cm) diameter by 5 (12.7 cm) inch long cylindrical ingots [1 lb (454 g)], and the two pound (908 g) trapezoidal ingots mentioned above. Slices of trapozoidal ingots are referred to in the following tables as trap slices and sl. traps.

The optimum size of the lithium metal employed will depend upon the size of the reaction being carried out. Generally, the size of the pieces of lithium being employed will be such that the overall reaction time will be less than 8–10 hours. The pieces of metal should be easily visible as being discrete particles, i.e., not particles produced by a dispersion process as described above [less than 0.1 millimeter].

Table I compares the sizes of some lithium metal pieces and their surface area per gram against the overall reaction time, including the feed time of the alcohol, and the run size. Note the longer overall reaction time for lithium dispersion versus bulk lithium [same size run].

Generally, it is preferable to use excesses of such bulk metal relative to the tert-butyl alcohol in the range of 2:1 to 10:1, but, most preferably, 3:1 to 5:1.

Feeding the tert-butyl alcohol gradually rather than adding it all to the reactor initially lengthens the reaction time somewhat, but not inordinately so. Essentially, the alcohol reacts about as quickly as it is added after the first run of a consecutive series is completed. It is thought that this first run of the series serves to condition the metal and acts much like the catalyst activation. Thus, the second run of such a series, where all of the alcohol is added at once, is completed in a period of 130 minutes (see Table III series 1), whereas, in a second run where the alcohol is added gradually over a period of 108 minutes, the reaction is complete in 155 minutes [see Table III, Series 2].

The reactions may be carried out at ordinary [atmospheric] pressure, but the atmospheric composition above the contents of the reaction vessel should be inert. Thus, the atmosphere should be dry and inert to lithium metal, i.e., most favorably be argon gas. Higher pressures, i.e., those above atmospheric, may be employed to raise the reaction temperature and thus, to further speed up the reaction.

Regardless of which size lithium pieces one employs, it is preferable to use a low sodium containing grade of lithium metal. Preferably, one should use a grade of lithium metal containing 0.001 to 0.6% by weight of sodium based on lithium; more preferable is a sodium level of less than 0.1%, and most preferable is a sodium level of 0.001 to 0.01 weight percent of the lithium metal. For example, employing lithium dispersion at a 1:1 level with tert-butyl alcohol in THF medium, at a sodium level of 0.002 wt %,. the reaction is essentially completed (>95%) in two to three hours time, whereas if the sodium level of the lithium metal used is 0.79 wt %, the reaction, to achieve above 90% completion, requires an additional 3–4 hours. The lithium metal in the latter case agglomerates to give larger pieces of less reactive lithium. At intermediate levels of sodium [0.19% and 0.38%] the reactions proceed more readily and are also completed in 2–3 hours [see Table II].

In the case of bulk metal, this effect is strikingly evident. Tables III and IV present data at low (<0.01 wt %) and high (>0.6 wt %) sodium levels in the lithium metal employed. At the lower sodium level, overall reaction times are of the order of 1.5 to 3 hours and the reactions are complete, yielding near quantitative conversions of lithium tert-butoxide, whereas at the higher sodium level, the reaction time is prohibitively slow and the reactions are incomplete. Obviously, sodium slows (inhibits) the reaction of bulk lithium with tert-butanol that a viable process is not possible. The sodium effect with bulk lithium metal is quite unexpected and converse to what is known about the preparation of other lithio organics, for example, alloyed sodium (0.5 to 1%) are known to speed initiations and increase reaction rates in the preparation of alkyl lithium compounds such as n-butyllithium, sec-butyllithium, tert-butyllithium, etc.

Catalysts are employed to speed up the overall rate of the reaction. These are generally lower molecular weight $C_1$ to $C_3$ alcohols, particularly methanol, ethanol, and isopropanol. Catalyst levels should be in the range of 2–10 mole % based on tert-butyl alcohol reactant, and most preferably, 3–7 mole %.

Table V presents results using these catalysts in runs with lithium metal rod pieces (1.27 cm diameter by 0.5 cm long). The overall reaction times are cut from 332 minutes (5.5 hours) to 180 to 218 minutes (3–3.6 hours) using 4–5 mole % of catalysts methanol, ethanol or isopropanol. Other higher alcohols ($C_4$ and greater) may be used, but do not generally give as good results.

Alcohol reactants other than tert-butyl alcohol can be employed, such as, for example, $C_4$–$C_{10}$ tertiary alkyl alcohols, such as, e.g., tert-amyl alcohol, 3-methyl-3-hexanol, 3-ethyl-3-pentanol, and 4-methyl-4-heptanol.

Solvents which may be used in the process of this invention to prepare lithium tert alkoxides are ethers such as ethyl ether, 1,2-dimethoxyethane, tetrahydrofuran, methyltetrahydrofuran, tetrahydropyran, and the like, and hydrocarbon solvents such as pentane, hexane, heptane, and toluene, and mixtures thereof. Although the most favored reaction temperature is the reflux temperature of the selected solvent, however, the reaction may be run below reflux, e.g., 40 to 100° C. depending on the boiling point of the solvent. However, the least favorable temperatures are below about 40–45° C.

The reaction concentration of the product alkoxide being formed is generally limited by the solubility of the product in the solvent being employed. For example, the solubility of lithium tert-butoxide in tetrahydrofuran is approximately 2.4 moles per liter of solution. The preferred reaction concentration, however, is somewhat less than this, i.e., about 2.0 moles per liter of solution. Thus, it is best to carry out these reactions at concentration levels as high as possible without at the same time fostering a condition of insolubility of the product.

The following examples further illustrate the invention.

Exemplary Runs of Lithium tert-Butoxide Employing Low Sodium (0.0035%) Bulk Lithium
[Table III, Series 1]

A volume of 426 milliliters of dry tetrahydrofuran and 76.71 grams [1.03 moles] of dry tert-butyl alcohol were added to a one liter three necked flask equipped with a mechanical stirrer, reflux condenser, thermometer, and gas inlet tube for provision of an argon atmosphere. The solution was heated to 61 degrees Centigrade and 24 pieces of lithium metal, cut into cubes with the approximate dimensions of one centimeter on each side [21.53 grams, 3.10 gram equivalents], added to the flask as rapidly as possible. Heating was continued to bring the mixture to reflux with stirring. After 30 minutes, a sample of the solution was taken [4.24 grams] and analyzed for alkalinity content and extent of conversion of the alcohol present in the reactor to product lithium alkoxide. Conversion at this point was 17.4%. Samples were taken at 60, 120, 150 and 180 minutes. Conversions were 37.6%, 84.4%, 92.6%, and 98.4%, respectively. After the 150 minute sample the metal pieces started losing their blue color and became shiny. At 180 minutes hydrogen evolution ceased and the heating was stopped. The shiny pieces were pitted. After the reaction mixture had cooled to room temperature, the slightly cloudy solution was decanted away from the unreacted excess lithium metal pieces and stored in an argon-flushed bottle. A weight of 7.9 grams of tert-butyl alcohol [0.1068 moles] was added to the bottle. To the remaining pieces of lithium metal in the reaction flask was added 439 milliliters of tetrahydrofuran. After standing overnight the solution contents of the bottle were clear.

Second Consecutive Run

To the above reactor, containing lithium and tetrahydrofuran, was added another eight pieces of lithium metal in the form of 1×1×1 centimeter [approximately] cubes [7.41 grams, 1.068 gram equivalents]. The reactor contents were heated to about 59° C. and a solution of 79.1 grams [1.069 moles] of tert-butyl alcohol and 50 milliliters of tetrahydrofuran added all at once. The mixture was stirred and heated to reflux and, once again, samples removed to determine the extent of conversion at definite time periods. At 20, 40, 100, and 130 minutes the conversions were 23%, 38%, 90%, and 99%, respectively. After cooling the reaction mass to room temperature the cloudy solution was decanted away from the remaining lithium metal into an argon-flushed bottle and 7.8 grams [0.1054 moles] of tert-butyl alcohol added to the bottle. A volume of 416 milliliters of tetrahydrofuran was added to the reactor containing the remaining lithium metal. After standing overnight the solution contents of the bottle were clear.

Third Consecutive Run

Another eight pieces of lithium metal [7.02 grams] in the form of cubes was added to the above reactor from the second consecutive run, the mix heated to 53.7° C., 75.42 grams of t-butyl alcohol added and the reaction continued at reflux. Samples taken at 20, 60, 90, and 124 minutes showed conversions of 20, 52, 82, and 100%, respectively. The product solution was decanted away from the metal as described above, and 432 ml of THF added to the remaining metal in the reactor.

Fourth Consecutive Run

Eight pieces, 7.29 grams of lithium were added to the reactor, the mix heated to 51.3° C., 77.8 grams of t-butyl alcohol added, and the reaction carried on at reflux. Conversions at 20, 40, 80, and 120 min were 26, 37, 72, and 100%, resp. The product solution was decanted away and 434 ml THF added to the reactor. The product solution was then filtered and a clear solution obtained with a filtration time of four minutes. The solids on the filter plate were washed with 104.2 grams of a solution of seven grams of t-butyl alcohol in tetrahydrofuran and dissolved completely indicating that they were undissolved lithium t-butoxide. Analysis of both clear solutions [main product and wash] showed recovered yields of 90.5% and 6.2%, resp. for a total yield of 96.7%, based on starting alcohol.

Fifth Consecutive Run

Eight pieces, 7.32 grams lithium added to reactor, mix heated to 62.9° C., 78.35 grams alcohol added, reaction heated to reflux. Conversions at 20, 40, 60, and 79 min were 39, 63, 87, and 96%. Product decanted and 421 ml THF added to reactor.

Sixth Consecutive Run

No further lithium metal added to this run. The mixture from the fifth consecutive run was heated to 55.9° C. and 76.21 grams of t-butyl alcohol added [1.03 moles] all at once. The mixture was heated to reflux. Conversions at 20, 60, 80, and 180 min were 16, 28, 69, and 96%, resp. Product decanted and 7.8 grams of alcohol added to cloudy solution. The remaining metal in the flask was covered with 421 ml of THF. The next day the solution in the bottle was clear.

Seventh Consecutive Run

No further metal was added to this run. There should be only enough metal to react with another charge of alcohol. The reactor contents were heated to 62° C. and 75.48 grams of alcohol added and then the reaction heated to reflux. Conversions at 60, 120, 180, 240, 270, 300 and 334 min were 35, 60, 83, 94.5, 95.7, 96.6 and 96.6%, resp.

Note 1.: It was found on larger [pilot plant] runs where overall reaction times were somewhat slower due to a greater proportionate size of the bulk metal employed [see Table I] that the product solutions generated from consecutive 3× metal runs were essentially clear at the end of the reactions and did not require any further addition of tert-alcohol and overnight standing to effect clarification.

Note 2.: The lithium metal used in these runs contained 0.0035% sodium.

Comparative Runs Employing Bulk Lithium Containing 0.74 Percent Sodium [Tavle IV, Series 3]

In these runs, three equivalents of lithium metal in the form of cubes were used as in consecutive exemplary runs above. The object of the experiment is to determine the relative overall reaction times when the bulk lithium metal contains an appreciable amount of alloyed sodium (re: Lentz).

In a reactor equipped as in the exemplary runs above a total of 75.7 grams of tert-butyl alcohol [1.02 moles] and 419 ml of tetrahydrofuran were heated to reflux and 21.2 grams (3.06 moles) of lithium metal in the form of 1×1×1 cm cubes added as quickly as possible. The mixture was heated and stirred at reflux and samples removed periodically to determine conversion. After 100, 220, 380 and 1320 minutes (22 hours), conversions of reactants to lithium tert-butoxide were 5, 23, 48, and 65%, respectively. After 22 hours hydrogen evolution was still evident. After the reaction mixture had cooled to room temperature, the slightly cloudy solution was decanted away from the unreacted excess lithium metal pieces and stored in an argon-flushed bottle. To the remaining pieces of lithium metal in the reaction flask was added 419 milliliters of tetrahydrofuran. After standing overnight the solution contents of the bottle were clear.

Second Consecutive Run

To the above reactor, containing lithium and tetrahydrofuran, was added another eight pieces of lithium metal in the form of 1×1×1 centimeter [approximately]

cubes [7.0 grams, 1.01 gram equivalents]. The reactor contents were heated to about 59° C. and a solution of 74.2 grams [1.01 moles] of tert-butyl alcohol and 50 milliliters of tetrahydrofuran added all at once. The mixture was stirred and heated to reflux and once again, samples removed to determine the extent of conversion at definite time periods. At 100, 220, and 340 minutes the conversions were 16%, 45% and 69%, respectively. After cooling the reaction mass to room temperature the cloudy solution was decanted away from the remaining lithium metal into an argon-flushed bottle. A volume of 415 milliliters of tetrahydrofuran was added to the reactor containing the remaining lithium metal. After standing overnight the solution contents of the bottle were clear.

Third Consecutive Run

Another eight pieces of lithium metal [7.0 grams] in the form of cubes was added to the above reactor from the second consecutive run. The mix heated to 53.7° C. and 74.9 grams of tert-butyl alcohol added and the reaction continued at reflux. Samples taken at 100, 220 and 340 minutes showed conversions of 16, 53 and 74%, respectively. The product solution was decanted away from the metal as described above.

Another series of run are given in Table III (series 3) employing bulk lithium metal cubes containing slightly less sodium (0.69%).

Thus, comparison of this experiment employing bulk lithium metal containing an appreciable amount of sodium with the exemplary runs shown above and in Table III prepared with bulk lithium metal containing traces of sodium stresses that sodium inhibits (slows) reaction and gives lower conversions to such an extent as to prohibit a viable process.

Comparative Single Run Employing Bulk Lithium [Table III]

In this run, only a single equivalent of lithium metal in the form of cubes is used instead of three equivalents as in consecutive runs 3–5 above. The object of the experiment is to determine the relative overall reaction times and also to compare the overall reaction time of this run with the seventh consecutive run above where only one equivalent of metal is used.

A solution of 84.57 grams of tert-butyl alcohol [1.141 moles] and 378 ml of tetrahydrofuran were heated to reflux and nine pieces [7.2 grams, 1.0375 g. eq] of lithium metal in the form of 1×1×1 cm cubes added as quickly as possible, The mixture was heated and stirred at reflux and samples removed periodically to determine conversion. At 60, 180, 300, 420 and 480 min conversions were 12, 35, 68, 91, and 97%, respectively.

Both the 3× equivalents run and the seventh consecutive run [above] were considerably faster than the comparative single run.

Comparative Runs Employing Lithium Dispersions [Table II]

Exemplary Run—The Preparation of Lithium t-Butoxide Using Low Sodium Containing Lithium Dispersion A weight of 27.7 grams of a 30 weight percent lithium dispersion, wherein the lithium metal contained 0.0148% sodium, was washed three times with dry hexane and once with dry pentane and then was blown dry with argon gas. The dry metal powder weighed 8.86 grams [1.276 moles]. The metal was transferred to a one liter three necked flask equipped as described above with the aid of most of a charge of 525 ml of dry THF and heated to reflux. A weight of 95.4 grams of tert-butyl alcohol was diluted with the remaining THF [ca 50 ml] and slowly added to the stirred contents of the flask from a dropping funnel over a 46 min period. No agglomeration of the metal was noted during the reaction. Samples for analysis were withdrawn through a syringe filter at 30, 60, and 100 minutes. Conversions were 93.7, 98.8, and 99.7%, respectively. A cloudy, white solution was obtained.

Another, similar run was made, using a lithium dispersion made from lithium metal containing less than 0.01% sodium [#8599]. Conversions after 15 and 135 min were 93 and 96%. The product solution required 2.5 hours to filter completely [slow filtration] compared to just several minutes for one of the bulk metal laboratory runs described above.

Comparative Run Using a High Sodium Containing Lithium Dispersion

A weight of 23.1 grams of a 30 weight percent lithium dispersion in mineral oil containing 6.93 grams [0.9986 gr. eq.] of lithium metal possessing a sodium content of 0.76% was transferred with the aid of 361 ml of dry THF to a one liter three necked flask equipped as above and heated to reflux. A solution of 81.4 grams [1.10 moles] of tert-butyl alcohol and 50 ml of dry THF was added to the contents of the flask over a 42 min period at reflux. The lithium metal particles agglomerated into bigger pieces. Samples of the product were filtered through a syringe filter and analyzed for total alkalinity. Conversions were 86.6% [30 min], 90% [55 min], 92.3% [115 min], 92.5% [235 min], and 95.1% [330 min].

Exemplary Run—The Preparation of Lithium t-Butoxide Employing Bulk Lithium and a Catalyst A weight of 81.3 grams [1.096 moles] of tert-butyl alcohol and 3.0 grams [0.05 moles] of isopropyl alcohol were mixed with 410 ml of tetrahydrofuran and heated to reflux [see apparatus description above].

A weight of 6.99 grams [1.007 moles] of lithium metal rods, 1.27 cm in diameter and one centimeter long was added to the refluxing solution all at once. The sodium content of the lithium metal was 0.0093%. The reaction was allowed to proceed for 30 minutes and a sample taken for total alkalinity in order to calculate the degree of conversion [39%]. Subsequent samples were taken at 60, 90, 120, 150 and 190 minutes, at which point there was no longer any hydrogen release noted. The degree of conversion for these last five samples were 68, 79, 89, 93, and 96%.

A number of runs are catalogued in Table V using different catalysts as well as a comparitive run with no catalyst.

TABLE 1

SYNTHESIS LTB IN THF EMPLOYING VARIOUS LITHIUM TYPES AND SIZES

| SITE | LITHIUM PIECES | LITHIUM DIMENSIONS | SURFACE AREA PER G LI (CM2/G) | RUN SIZE MOLES | REACTION TIME-HRS. |
|---|---|---|---|---|---|
| LAB | DISP (1) | 10 micron | 3770 | | |
|  | DISP (1) | 20 micron | 1887 | 1 | 2 |
|  | DISP (1) | 100 micron | 1130 | | |
| LAB | CUBE (2) | 1 cm × 1 cm × 1 cm | 8.1 | 1 | 2 |
| LAB | ROD (2) | 1.27 cm diax 1 cm | 9.7 | 1 | 1.5 |
| P.P. | TRAP SLICES (2) | 8.9 cm/6.35 cm × 8.26 cm × 2.54 cm | 2.7 | 184 | 4 to 5 |

(1) Mole ratio Lithium/t-butanol = 1
(2) Mole ratio Lithium/t-butanol = 3

TABLE II

SYNTHESIS OF LTB IN REFLUXING THF EMPLOYING LITHIUM DISPERSION

| | REAGENTS | | | | CONDITIONS | | RESULTS | | |
|---|---|---|---|---|---|---|---|---|---|
| | LITHIUM | | TBA (1) | THF | TEMP | TBA Feed | CONC. (2) | CONV. (3) | TIME (4) |
| EXP. No | % Na | MOLE | LI/TBA MOLES | MLS | ° C. | MIN. | M. | % | MIN. |
| 8622 | 0.015 | 1.28 | 0.91 1.40 | 525 | reflux (5) | 46 | 18.3 | 98.8 | 106 |
| 8617 | 0.190 | 1.52 | 0.91 1.68 | 627 | reflux | 45 | 17.9 | 98.0 | 145 |
| 8620 | 0.380 | 1.22 | 0.91 1.34 | 501 | reflux | 45 | 16.2 | 100.0 | 165 |
| 8601 | 0.760 | 1.00 | 0.91 1.10 | 411 | reflux | 42 | 17.6 | 95.1 | 372 |

(1) TBA = t-Butyl Alcohol
(2) Concentration (molarity) at end of run.
(3) Percent conversion at end of run. Based on lithium.
(4) Time to complete reaction. Includes TBA feed time.
(5) Reflux = 67 to 68° C.

TABLE III

SYNTHESIS OF LTB IN REFLUXING THF EMPLOYING BULK LITHIUM
LITHIUM CUBES - 1 CM SQUARE

| | REAGENTS | | | | CONDITIONS | | RESULTS | | |
|---|---|---|---|---|---|---|---|---|---|
| | LITHIUM | LI/TBA | TBA (1) | THF | Rx. TEMP | TBA Feed | CONC. (2) | CONV. (3) | TIME (4) |
| EXP. No. | % Na MOLE | MOLE RATIO | MOLES | ml | ° C. | min | M. | % | MIN. |
| SERIES 1 | | | | | | | | | |
| 8435 | 0.0035 3.10 | 3.0 | 1.03 | 425 | reflux (5) | 0 | 18.5 | 98.4 | 180 |
| 8441 | 0.0035 1.07 | 3.2 | 1.07 | 439 | reflux | 0 | 18.4 | 98.7 | 130 |
| 8443 | 0.0035 1.01 | 3.1 | 1.01 | 416 | reflux | 0 | 18.7 | 100.0 | 120 |
| 8446 | 0.0035 1.05 | 3.3 | 1.05 | 432 | reflux | 0 | 18.6 | 100.0 | 120 |
| 8453 | 0.0035 1.05 | 3.4 | 1.06 | 434 | reflux | 0 | 17.9 | 96.0 | 79 |
| 8454 | 0.0035 0.00 | 2.2 | 1.02 | 421 | reflux | 0 | 17.9 | 95.8 | 180 |
| 8459 | 0.0035 0.00 | 1.2 | 1.02 | 421 | reflux | 0 | 18.7 | 96.6 | 300 |
| | TOTAL LI 7.28 | TOTAL | 7.26 | | | | AVG. Y | 97.9 | |
| SERIES 2 | | | | | | | | | |
| 8476 | 0.0035 3.05 | 2.9 | 1.07 | 439 | reflux | 129 | 17.9 | 97.8 | 310 |
| 8477 | 0.0035 1.02 | 3.0 | 1.02 | 419 | reflux | 108 | 17.9 | 97.8 | 155 |

TABLE III-continued

SYNTHESIS OF LTB IN REFLUXING THF EMPLOYING BULK LITHIUM
LITHIUM CUBES - 1 CM SQUARE

| | REAGENTS | | | | | CONDITIONS | | RESULTS | | |
|---|---|---|---|---|---|---|---|---|---|---|
| | LITHIUM | | LI/TBA | TBA (1) | THF | Rx. TEMP | TBA Feed | CONC. (2) | CONV. (3) | TIME (4) |
| EXP. No. | % Na | MOLE | MOLE RATIO | MOLES | ml | ° C. | min | M. | % | MIN. |
| 8478 | 0.0035 | 1.01 | 3.0 | 1.01 | 414 | reflux | 106 | 17.8 | 97.2 | 140 |
| 8482 | 0.0035 | 0.98 | 2.9 | 0.98 | 404 | reflux | 120 | 18 | 98.1 | 145 |
| | TOTAL LI | 6.06 | TOTAL | 4.08 | | | | AVG. Y | 97.7 | |
| SERIES 3 | | | | | | | | | | |
| 8527 | 0.69 | 3.06 | 3.0 | 1.02 | 41 9 | reflux | 0 | 11.9 | 63.6 | 370 |
| 8534 | 0.69 | 1.01 | 3.3 | 1.01 | 416 | reflux | 0 | 14.4 | 76.4 | 410 |
| 8537 | 0.69 | 1.01 | 4.4 | 1.01 | 415 | reflux | 0 | 15.01 | 80.5 | 400 |
| | TOTAL LI | 5.08 | TOTAL | 3.04 | | | | AVG. Y | 73.5 | |
| COMPARATIVE SINGLE RUN | | | | | | | | | | |
| 8434 | 0.0035 | 1.04 | 0.91 | 1.14 | 427 | reflux | 0 | 17.1 | 96.7 | 480 |

(1) TBA = t-Butyl Alcohol
(2) Concentration (Molarity) at end of run.
(3) Percent conversion at end of run. Based on lithium.
(4) Time to complete reaction.
(5) Reflux = 67 to 68° C.

TABLE IV

SYNTHESIS OF LTB IN REFLUXING THF EMPLOYING BULK LITHIUM
LITHIUM RODS - 0.5" DIA × 1 CM LONG

| | REAGENTS | | | | | CONDITIONS | | RESULTS | | |
|---|---|---|---|---|---|---|---|---|---|---|
| | LITHIUM | | LI/TBA | TBA (1) | THF | Rx. TEMP | TBA Feed | CONC. (2) | CONV. (3) | TIME (4) |
| EXP. No. | % Na | MOLE | MOLE RATIO | MOLES | ml | ° C. | min | M. | % | MIN. |
| SERIES 1 | | | | | | | | | | |
| 8396 | <0.01 | 2.97 | 2.72 | 1.09 | 407 | reflux (5) | 0 | 19.2 | 103.4 | 215 |
| 8397 | <0.01 | 0.99 | 2.96 | 1.09 | 407 | reflux | 0 | 19.3 | 105.3 | 153 |
| 8403 | <0.01 | 1.00 | 2.98 | 1.10 | 411 | reflux | 0 | 18.4 | 97.4 | 100 |
| 8404 | <0.01 | 1.00 | 2.98 | 1.10 | 411 | reflux | 0 | 18.4 | 101.4 | 60 |
| | TOTAL LI | 5.96 | TOTAL | 4.38 | | | | AVG. Y | 101.88 | |
| SERIES 2 | | | | | | | | | | |
| 8436 | <0.01 | 3.03 | 3.00 | 1.01 | 415 | reflux | 0 | 18.6 | 98.7 | 240 |
| 8442 | <0.01 | 1.03 | 2.93 | 1.04 | 424 | reflux | 0 | 18.3 | 98.5 | 90 |
| 8444 | <0.01 | 1.01 | 2.99 | 1.01 | 417 | reflux | 0 | 18.3 | 98.3 | 120 |
| 8447 | <0.01 | 1.03 | 2.95 | 1.03 | 424 | reflux | 0 | 18.1 | 96.5 | 102 |
| 8452 | <0.01 | 1.07 | 2.88 | 1.07 | 439 | reflux | 0 | 17.9 | 96.9 | 72 |
| 8455 | <0.01 | 1.02 | 2.97 | 1.02 | 420 | reflux | 0 | 18.1 | 97.3 | 116 |
| 8460 | <0.01 | 0.96 | 3.08 | 0.97 | 397 | reflux | 0 | 17.6 | 94.8 | 70 |
| 8461 | <0.01 | 0.95 | 3.12 | 0.95 | 389 | reflux | 0 | 18.4 | 98.4 | 105 |
| 8462 | <0.01 | 0.96 | 3.08 | 0.96 | 396 | reflux | 0 | 17.7 | 95.7 | 65 |
| 8464 | <0.01 | 1.03 | 2.95 | 1.03 | 424 | reflux | 0 | 20.5 | 95.0 | 80 |
| 8466 | <0.01 | 0.00 | 1.99 | 1.01 | 420 | reflux | 0 | 18.8 | 99.3 | 120 |
| 8467 | <0.01 | 0.00 | 0.97 | 1.03 | 432 | reflux | 0 | 17.4 | 92.5 | 221 |
| | TOTAL LI | 12.09 | TOTAL | 12.12 | | | | AVG. Y | 96.83 | |
| SERIES 3 | | | | | | | | | | |
| 8505 | 0.74 | 3.17 | 2.99 | 1.06 | 434 | reflux | 0 | 12.1 | 64.9 | 380 |
| 8511 | 0.74 | 1.05 | 3.36 | 1.05 | 434 | reflux | 0 | 12.7 | 68.8 | 340 |
| 8513 | 0.74 | 0.97 | 3.90 | 0.97 | 398 | reflux | 0 | 13.8 | 74.4 | 340 |
| | TOTAL LI | 5.19 | TOTAL | 3.08 | | | | AVG. Y | 69.37 | |

TABLE IV-continued

SYNTHESIS OF LTB IN REFLUXING THF EMPLOYING BULK LITHIUM
LITHIUM RODS - 0.5" DIA × 1 CM LONG

| | REAGENTS | | | | | CONDITIONS | | RESULTS | | |
|---|---|---|---|---|---|---|---|---|---|---|
| | LITHIUM | | LI/TBA | TBA (1) | THF | Rx. TEMP | TBA Feed | CONC. (2) | CONV. (3) | TIME (4) |
| EXP. No. | % Na | MOLE | MOLE RATIO | MOLES | ml | ° C. | min | M. | % | MIN. |
| COMPARATIVE SINGLE RUN | | | | | | | | | | |
| 8291 | 0.009 | 1.03 | 0.94 | 1.10 | 370 | reflux | 0 | 18.1 | 97.1 | 332 |

(1) TBA = t-Butyl Alcohol
(2) Concentration (Molarity) at end of run.
(3) Percent conversion at end of run. Based on lithium.
(4) Time to complete reaction.
(5) Reflux = 67 to 68° C.

TABLE V

SYNTHESIS OF LTB IN REFLUXING THF EMPLOYING BULK LITHIUM AND CATALYSTS
LITHIUM RODS

| | REAGENTS | | | | | CATALYST | | CONDITIONS | | | RESULTS | | |
|---|---|---|---|---|---|---|---|---|---|---|---|---|---|
| EXP. | LITHIUM | | | TBA (1) | | | MOLE % | THF | Rx. TEMP | TBA Feed | CONC. (2) | CONV. (3) | TIME (4) |
| No | TYPE | % Na | MOLES | LI/TBA | MOLES | TYPE | (5) | ml | ° C. | min | M. | % | MIN. |
| 8311 | ROD (7) | 0.009 | 1.03 | 0.94 | 1.10 | methano | 5.14 | 410 | reflux (6) | 0 | 18.1 | 97.5 | 218 |
| 8330 | ROD (7) | 0.009 | 1.02 | 0.91 | 1.12 | methano | 2.51 | 410 | reflux | 0 | 18.1 | 98.0 | 233 |
| 8334 | ROD (7) | 0.009 | 1.06 | 0.97 | 1.09 | methano | 0.81 | 410 | reflux | 0 | 18.8 | 98.0 | 332 |
| 8337 | ROD (8) | 0.009 | 0.98 | 0.89 | 1.10 | methano | 4.30 | 410 | reflux | 0 | 17.4 | 97.5 | 250 |
| 8351 | ROD (7) | 0.009 | 1.01 | 0.93 | 1.09 | isopropano | 5.03 | 410 | reflux | 0 | 17.7 | 96.0 | 180 |
| 8364 | ROD (7) | 0.009 | 1.02 | 0.90 | 1.13 | isopropano | 4.80 | 410 | 45 | 0 | 16.4 | 91.0 | 330 |
| 8365 | ROD (7) | 0.009 | 1.02 | 0.94 | 1.09 | isopropano | 4.79 | 410 | 55 | 0 | 18.1 | 97.0 | 330 |
| 8378 | ROD (7) | 0.009 | 1.02 | 0.94 | 1.08 | isobutano | 5.00 | 410 | reflux | 0 | 17.0 | 92.0 | 269 |
| 8386 | ROD (7) | 0.009 | 0.99 | 0.91 | 1.09 | n-octanol | 4.90 | 410 | reflux | 0 | 12.6 | 73.0 | 300 |
| 8390 | ROD (7) | 0.009 | 0.96 | 0.88 | 1.09 | ethano | 4.30 | 410 | reflux | 0 | 16.7 | 97.0 | 180 |
| 8391 | ROD (7) | 0.009 | 0.99 | 0.89 | 1.11 | s-butano | 4.71 | 405 | reflux | 0 | 19.4 | 100.0 | 330 |
| COMPARATIVE SINGLE RUN NO CATALYST | | | | | | | | | | | | | |
| 8291 | ROD (7) | 0.009 | 1.03 | 0.94 | 1.10 | NONE | NONE | 370 | reflux | 0 | 18.1 | 97.1 | 332 |

(1) TBA = t-Butyl Alcohol
(2) Concentration (molarity) at end of run.
(3) Percent conversion at end of run. Based on lithium.
(4) Time to complete reaction
(5) Based on TBA.
(6) Reflux = 67 to 68° C.
(7) Lithium rod 0.5" dia. × 1 cm
(8) Lithium rod 0.5" dia. × 4.6 cm

TABLE VI

SYNTHESIS OF LTB IN REFLUXING THF EMPLOYING BULK LITHIUM - SCALE-UP
LITHIUM TRAPS-CUT INTO 10 SLICES-8.9 CM/6.35 CM(WIDTH) × 8.26 CM(HT.) × 2.54 CM(THICK)

| | REAGENTS | | | | | | CONDITIONS | | RESULTS | | |
| | LITHIUM | | | | TBA (1) | THF | TEMP | TBA Feed | CONC. (2) | CONV. (3) | TIME (4) |
| RUN NO | TYPE | % Na | MOLES | LI/TBA | MOLES | LBS. | °C. | HRS | M. | % | MIN. |
|---|---|---|---|---|---|---|---|---|---|---|---|
| P.P SERIES (6) | | | | | | | | | | | |
| 9302 | SL. TRAPS | 0.0035 | 523 | 2.84 | 184 | 133.0 | reflux (5) | 1.5 | 18.9 | 93.7 | 435 |
| 9303 | SL. TRAPS | 0.0035 | 196 | 2.91 | 184 | 148.0 | reflux | 1.3 | 17.9 | 97.2 | 355 |
| 9304 | SL. TRAPS | 0.0035 | 183 | 2.90 | 184 | 148.0 | reflux | 1.3 | 18.1 | 97.1 | 265 |
| 9305 | SL. TRAPS | 0.0035 | 196 | 3.00 | 182 | 148.0 | reflux | 1.2 | 17.3 | 94.1 | 300 |
| 9306 | SL. TRAPS | 0.0035 | 183 | 3.01 | 182 | 148.3 | reflux | 0.8 | 18.1 | 97.0 | 325 |
| 9307 | SL. TRAPS | 0.0035 | 183 | 3.01 | 182 | 148.3 | reflux | 0.7 | 18.6 | 99.4 | 210 |
| 9308 | SL. TRAPS | 0.0035 | 183 | 3.02 | 182 | 148.3 | reflux | 1.2 | 18.7 | 96.7 | 230 |
| 9309 | SL. TRAPS | 0.0035 | 0 | 1.70 | 216 | 174.8 | reflux | 1.5 | 20.4 | 100.0 | 210 |
| 9310 | SL. TRAPS | 0.0035 | 0 | 0.70 | 216 | 174.8 | reflux | 1.5 | 9.0 | 48.2 | 620 |
| | | TOTAL Li | 1647 | TOTAL TBA | 1712 | | | | | | |

(1) TBA = t-Butyl Alcohol
(2) Concentration (molarity) at end of run.
(3) Percent conversion at end of run. Based on lithium.
(4) Time to complete reaction.
(5) Reflux = 67 to 68° C.
(6) Pilot plant runs

What is claimed is:

1. A solution of lithium tert-alkoxide in a solvent selected from the group consisting of etheral solvents, hydrocarbon solvents, and mixtures thereof wherein the sodium content is less than 10 ppm.

2. A solution of lithium tert-butoxide in tetrahydrofuran wherein the sodium content is less than 1 ppm.

3. A solution of lithium tert-alkoxide in a solvent selected from the group consisting of ethereal and hydrocarbon solvents and mixtures thereof, said solution prepared by reacting lithium metal having a sodium content between 0.001 and 0.01 weight percent with a tertiary alcohol, wherein the sodium content of said solution is limited to the sodium content of the lithium metal reacted with the tertiary alcohol.

4. The solution of claim 3, wherein said lithium metal is reacted with said tertiary alcohol in the presence of a catalytically effective amount of a C1–C3 alcohol catalyst.

5. The solution of claim 4, wherein said solution is prepared in the presence of from about 2 to about 10 mole percent of said C1–C3 alcohol catalyst based on said tertiary alcohol.

6. A solution for preparing lithium tert-alkoxide comprising a solvent selected from the group consisting of etheral and hydrocarbon solvents and mixtures thereof, a bulk lithium metal having a sodium content between 0.001 and 0.01 weight percent, and a tertiary alcohol.

7. The solution of claim 6, further comprising a catalytically effective amount of a C1–C3 alcohol catalyst.

8. The solution of claim 7, wherein said C1–C3 alcohol catalyst is present in an amount of from about 2 to about 10 mole percent.

9. A solution of lithium tert-alkoxide in a solvent selected from the group consisting of etheral and hydrocarbon solvents and mixtures thereof, comprising bulk lithium metal having a sodium content between 0.001 and 0.01 weight percent.

* * * * *